United States Patent [19]

Schumann

[11] Patent Number: Plant 5,992

[45] Date of Patent: May 19, 1987

[54] GERANIUM PLANT NAMED CABARET

[75] Inventor: Ingeborg Schumann, Bad Ems, Fed. Rep. of Germany

[73] Assignee: Fischer Geraniums, Inc., Curacao, Netherlands Antilles

[21] Appl. No.: 761,013

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Jeffery, Schwaab, Mack, Blumenthal & Evans Schwartz

[57] ABSTRACT

A geranium plant named Cabaret having dark salmon flower color; semi-double flower form with large flowerhead; dark green foliage; fast rooting; compact growth habit; very good chlorophyll quality for transportation; and good weather resistance.

1 Drawing Figure

The present invention comprises a new and distinct cultivar of geranium, botanically known as *Pelargonium zonale,* and hereinafter referred to by the cultivar name Cabaret.

Cabaret is a product of a planned breeding program which had the objective of creating new geranium cultivars having dark green foliage, unique flower color, very good chlorophyll quality for shipping, very fast rooting, and compact growth habit.

Cabaret was originated from a hybridization made by Ingeborg Schumann in a controlled breeding program in Hillscheid, Federal Republic of Germany in 1981. The female parent was an inbred line of Regina. The male parent of Cabaret was the cultivar Bern of the "Pelfi" ® series of Pelargonien-Fischer KG, Hillscheid, Federal Republic of Germany. Both parents are unpatented.

Cabaret was discovered and selected as one flowering plant within the progeny of the stated cross by Ingeborg Schumann on June 4, 1982 in a controlled environment in Hillscheid, Federal Republic of Germany.

The first act of asexual reproduction of Cabaret was accomplished when vegetative cuttings were taken from the initial selection in January of 1983 in a controlled environment in Hillscheid, Federal Republic of Germany by a technician working under formulations established and supervised by Ingeborg Schumann. Horticultural examination of selected units initiated in the spring of 1983 and 1984 has demonstrated that the combination of characteristics as herein disclosed for Cabaret are firmly fixed and are retained through successive generations of asexual reproduction.

Cabaret has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Cabaret, which in combination distinguish this geranium as a new and distinct cultivar.

1. Dark salmon to orange-red flower color.
2. Semi-double flower form with large flowerhead.

3. Dark green foliage.
4. Very good chlorophyll quality for transportation.
5. Very fast rooting.
6. Compact growth habit.
7. Good weather resistance.

The accompanying photographic drawing shows typical flower and foliage characteristics of Cabaret, with colors being as true as possible with illustrations of this type.

In the following description color references are made to The Royal Horticultural Society Colour Chart. The color values were determined between 10:00 a.m. and 11:00 a.m. on May 22, 1985 under 35,000 Lux light intensity at Hillscheid, Federal Republic of Germany.

Classification:

*Botanical.*—A hybrid of the genus *Pelargonium l'hert* and species *Pelargonium zonale.*

*Commercial.*—Cabaret.

INFLORESCENCE

A. Umbel:

*Average diameter.*—118 mm.
*Average depth.*—61 mm.
*Peduncle length.*—156 mm.
*Pedicel length.*—32 mm.

B. Corolla:

*Average diameter.*—50 mm.
Form.—Semi-double; asymmetric.
*Color (general tonality from a distance of three meters).*—Dark salmon. Upper surface: 34A with white throat; fading to 34B-C.

C. Bud:

*Shape.*—Round to oval.
*Color.*—Light salmon; marbled red.

D. Reproductive organs:

*Androecium.*—Some sterile; some with 6 to 8 stamens.
*Gynoecium.*—4–5 lobed stigma.

E. Spring flowering response period: In Hillscheid, Federal Republic of Germany, in 1983, 60% of plants opened with at least one flower 13 weeks after planting of unrooted cuttings.

F. Outdoor flower production: The total flower count in 1983 in Hillscheid, Federal Republic of Germany, was between 42 and 45 flowers per plant for the June through October observation period.

G. Durability: Very good.

PLANT

A. Foliage:

*Form.*—Kidney shaped.

*Margin.*—Finely serrated; generally round tips.

*Color.*—Top surface: Dark g :en. Zonation: Medium green, weak zonation.

*Tolerance of botrytis.*—Good.

B. General appearance and form:

*Internode length.*—23 mm.

*Branching pattern.*—2.9 branches per plant.

*Height.*—210 mm.

I claim:

1. A new and distinct cultivar of geranium named Cabaret, as described and illustrated, and particularly characterized by its dark salmon flower color; semi-double flower form with large flower head; dark green foliage; fast rooting; compact growth habit; very good chlorophyll quality for transportation; and good weather resistance.

* * * * *

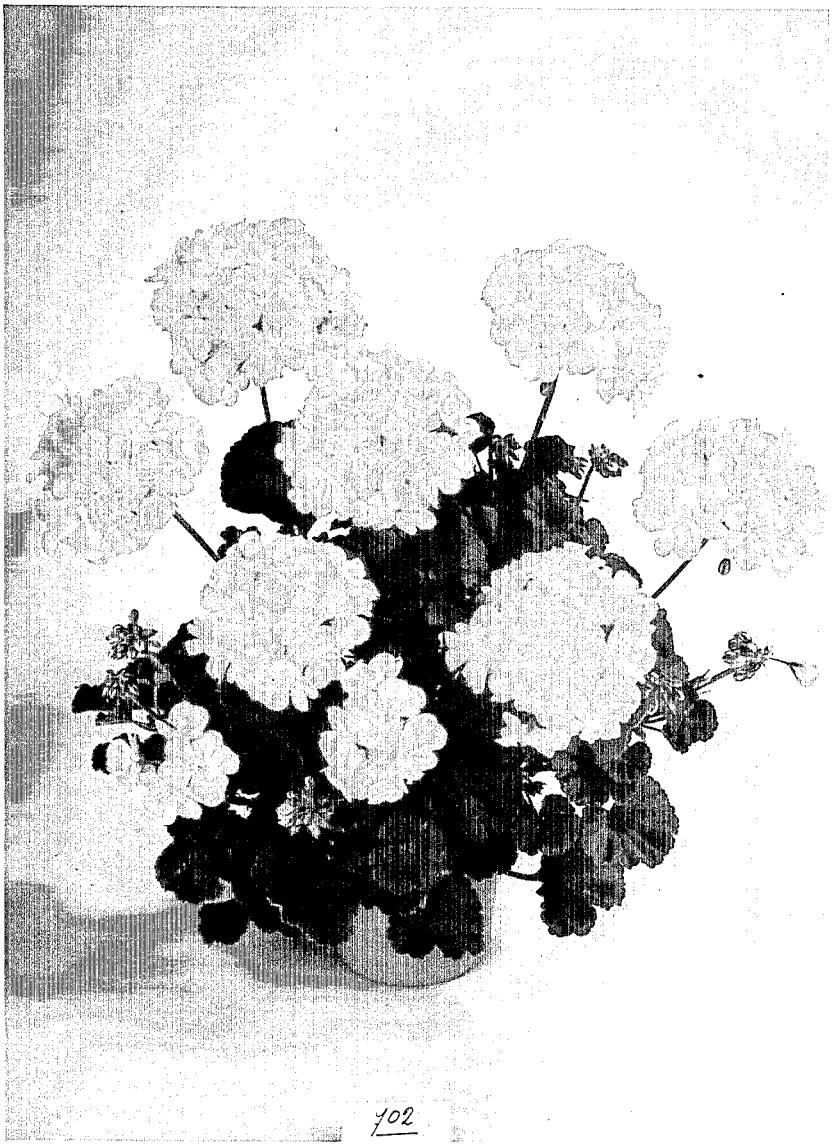
102